US006767359B2

(12) United States Patent
Weadock

(10) Patent No.: US 6,767,359 B2
(45) Date of Patent: Jul. 27, 2004

(54) PROSTHESIS FOR THE REPAIR OF THORACIC OR ABDOMINAL AORTIC ANEURYSMS AND METHOD THEREFOR

(75) Inventor: Kevin Shaun Weadock, Princeton, NJ (US)

(73) Assignee: Ethicon, Inc., Somerville, NJ (US)

( * ) Notice: Subject to any disclaimer, the term of this patent is extended or adjusted under 35 U.S.C. 154(b) by 216 days.

(21) Appl. No.: 09/968,482

(22) Filed: Sep. 28, 2001

(65) Prior Publication Data

US 2003/0065385 A1 Apr. 3, 2003

(51) Int. Cl.[7] ............................................... A61F 02/06
(52) U.S. Cl. ..................................... 623/1.14; 623/1.36
(58) Field of Search ............................ 623/1.13, 1.14, 623/1.36, 1.12, 1.23

(56) References Cited

U.S. PATENT DOCUMENTS

| 5,456,713 | A | | 10/1995 | Chuter | |
|---|---|---|---|---|---|
| 5,489,295 | A | * | 2/1996 | Piplani et al. | 623/1.35 |
| 5,522,881 | A | * | 6/1996 | Lentz | 623/1.13 |
| 5,628,783 | A | | 5/1997 | Quiachon et al. | |
| 5,700,269 | A | | 12/1997 | Pinchuk et al. | |
| 5,755,778 | A | * | 5/1998 | Kleshinski | 623/1.13 |
| 5,800,540 | A | | 9/1998 | Chin | |
| 6,004,347 | A | | 12/1999 | McNamara et al. | |
| 6,017,364 | A | | 1/2000 | Lazarus | |
| 6,030,413 | A | | 2/2000 | Lazarus | |
| 6,309,345 | B1 | * | 10/2001 | Stelzer et al. | 600/106 |

FOREIGN PATENT DOCUMENTS

| EP | 1 086 663 A1 | 3/2001 |
|---|---|---|
| EP | 1 086 664 A2 | 3/2001 |
| EP | 1 086 665 A1 | 3/2001 |

OTHER PUBLICATIONS

Dion, Y., et al., "Experimental Laparoscopic Aortobifemoral Bypass with End–to–Side Aortic Anastomosis", Surgical Laparoscopy & Endoscopy, vol. 9, No. 1, pp. 35–38.
Dion, Y., et al., "A new technique for laparoscopic aortobifemoral grafting in occlusive aortoiliac diease", Journal Vascular Surgery, vol. 26, No. 4, pp. 685–669.

\* cited by examiner

Primary Examiner—Corrine McDermott
Assistant Examiner—Thomas J Sweet

(57) ABSTRACT

An prosthesis for the repair of thoractic or abdominal aortic aneurysms (AAA) and a method for utilizing the prosthesis. Furthermore, an arrangement and method is provided for the repair of aortic aneurysms incorporating a device for the placement of the prosthesis in the corporeal lumen or body vessel of a patient, and wherein the prosthesis comprises a graft facilitating the exclusion of the aneurysm, and also provides for anastomotic structure for the attachment of the prosthesis in a laparoscopic surgical procedure.

15 Claims, 2 Drawing Sheets

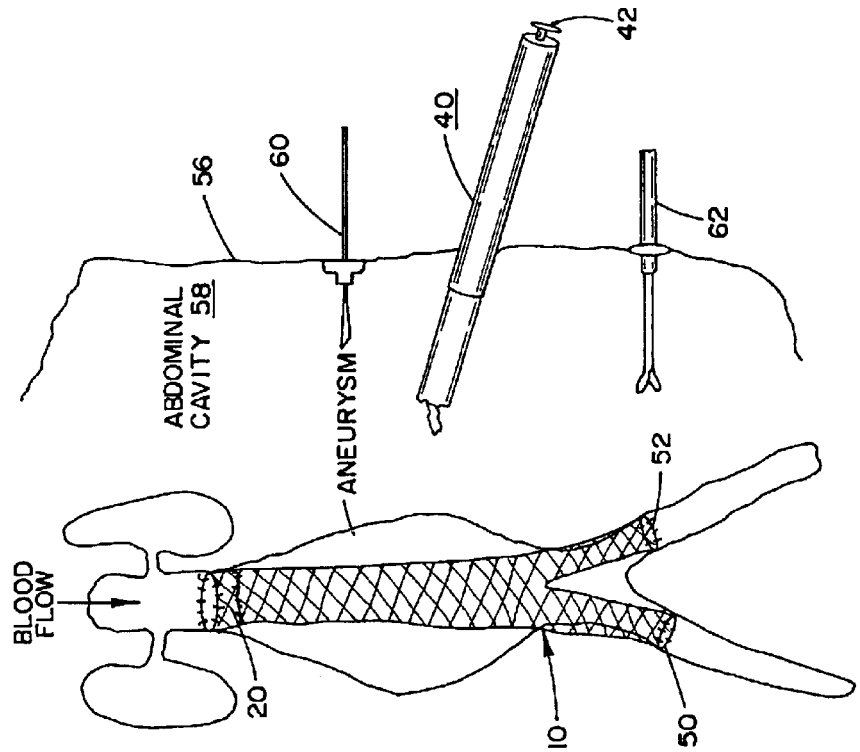
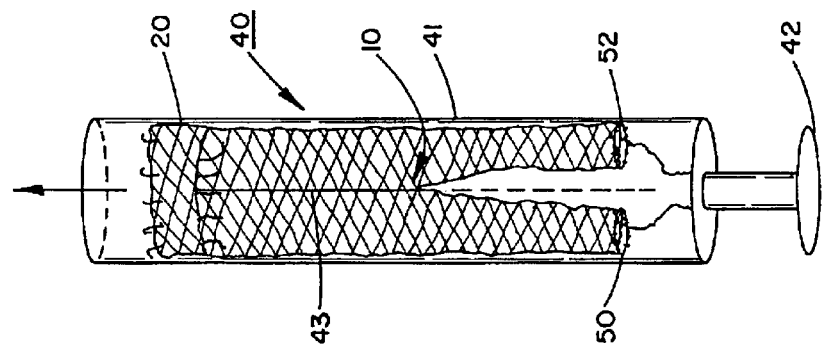

PROSTHESIS FOR THE REPAIR OF THORACIC OR ABDOMINAL AORTIC ANEURYSMS AND METHOD THEREFOR

BACKGROUND OF THE INVENTION

1. Field of the Invention

The present invention relates to a prosthesis for the repair of thoracic or abdominal aortic aneurysms (AAA) and to a method for utilizing the prosthesis. Furthermore, the invention is also directed to the provision of an arrangement and method for the repair of aortic aneurysms incorporating a device for the placement of the prosthesis in the corporeal lumen or body vessel of a patient, and wherein the prosthesis comprises a graft facilitating the exclusion of the aneurysm, and also provides for anastomotic structure for the attachment of the prosthesis in a laparoscopic surgical procedure.

It is a well established medical fact that various fluid conducting body or corporeal lumens, such as veins and arteries, may deteriorate or suffer trauma over time so that repair thereof becomes necessary. For example, various types of aneurysms or other deteriorative diseases may affect the ability of the lumen to conduct fluids, such as adequate blood flow, and in turn may create life-threatening situations. In some cases, the damaged lumen is repairable only with the use of a prosthesis, such as an artificial vessel or graft constituting a replacement vessel or a bypass.

For example, an aneurysm is a localized dilatation or weak spot in a blood vessel, whereby abdominal aortic aneurysms (AAA) are one of the most common and serious types of aneurysms. They are deemed by physicians to be atherosclerotic in origin, in effect, related to a high fat diet, high blood pressure, and cigarette smoking, although genetic factors that control collagen and/or elastic tissue metabolism may also be involved in such conditions.

In the implementation of the repair of vital vessels, such as the aorta, surgical repair is significantly life-threatening. Surgical techniques which are presently known in the art involve major surgery in which a graft resembling the natural vessel is spliced into the diseased or obstructed section of the natural vessel. Known procedures include surgically bypassing the damaged or diseased portion of the vessel and inserting an artificial or donor graft which is attached to the native vessel by an anastomosis.

It is also known within the confines of the medical profession to provide a prosthesis for the intraluminal repair of a vessel, such as an abdominal aorta having an aneurysm. The art has taught it to be expedient to provide a prosthesis which is positioned in a vessel, and then securing the prosthesis within the vessel with hooks or staples that are mechanically extended by the user. The early prior art devices were large in diameter, mechanically complex and, in turn, were susceptible to mechanical failure. Prior intraluminal grafting systems have embodied capsule catheters or balloon catheters, but these were relatively stiff and of a relatively high profile. Similarly, the prior art systems were configured in such a way that the graft was relatively difficult to deploy in the correct position. In addition, prior systems having a capsule catheter assembly were usually configured such that the prostheses was disposed within a unitary capsule. Further, the prior prosthesis were sometimes ill suited to withstand the high pressures existing in the vessels and, consequently, experienced structural failures.

Conventional repair of abdominal aortic aneurysms (AAA) involves exclusion of the aneurysm by implantation of bifurcated or straight vascular prostheses via a full laparotomy. This procedure has a high morbidity and mortality rates of 1–3%. Recent advances in engineering have resulted in stent-graft "prosthesis", delivered to the aneurysm via the femoral artery. This procedure requires a 18–24 F catheter to be placed in the femoral artery, then worked through the iliac artery to the aneursym, where the stent-graft is deployed. Problems associated with this technology include failure to exclude the aneurysm ("endoleak"), generation of microemboli as the device traverses calcified and tortuous peripheral arteries, device migration, and frequent emergency conversions to an open surgical procedure. Another difficulty associated with this technology is the need to have two devices placed, one for the aorta-iliac and one for the contralateral iliac. This requires two arterial access sites and may increase the likelihood of endoleak, since the junction of the aortoiliac and contralateral iliac is not a closed seal. There have also been attempts to repair AAA by laparoscopic techniques. This procedure may require up to 9 hours to complete, can result in paraplegia, and is also prone to emergency conversion to a laporotomy or open repair.

With regard to the prior art, although significant steps have been taken to provide methods and devices for deploying intralumenally grafts and the use of anastomotic means in order to bypass abdominal aortic aneurysms (AAA), many of these devices are still subject to difficulties due to utilizing catheters or extensive surgical procedures in contrast with laparoscopic surgery which replaces the highly invasive procedures of open surgery which are subjective to high mortality rates especially for elderly and seriously-ill patients.

2. Discussion of the Prior Art

Quiachon et al., U.S. Pat. No. 6,039,758 and U.S. Pat. No. 5,628,783 disclose bifurcated vessel grafts with spring-hook attachment structure at an end portion thereof, employed for a method of repairing an aneurysm in a vessel at a remote location. This necessitates the use of catheters and extensive surgery wherein a separate vessel engaging members are preattached to the graft but which do not contemplate the unique anastomotic devices attached to the graft prior to the emplacement of the prosthesis as described by the present invention.

Pierce, U.S. Pat. No. 6,152,956 discloses an endovascular prosthesis for repair of abdominal aortic aneurysms (AAA), and which includes a graft with an elastic wire means for connecting an end portion of the graft to the wall of the aorta.

McNamara et al., U.S. Pat. No. 6,004,347 discloses a fabric graft with a resilient anchor structure located at the end portions of the graft repairing an abdominal aortic aneurysm. A catheter-like a device which includes a dilator is provided to deploy the graft. This clearly precludes the utilization of laparoscopic surgery which also avoids the necessary for open surgery potentially leading to higher patient mortality rates.

Chin, U.S. Pat. No. 5,800,540 discloses a method and an apparatus for implementing endoscopic grafting; however, the patent does not disclose a graft including the novel anastomotic attachments at the ends of the graft and the unique system for the emplacement thereof.

Pinchuk et al., U.S. Pat. No. 5,700,269 discloses an endoluminal prosthesis deployment device which includes a dilator tip and a plunger. Again, as in the previously described publications, there is no disclosure of the unique prosthesis for the repair of thoracic or abdominal aorta aneurysms in a laparoscopic procedure and the unique device for the emplacement of the prosthesis.

Chuter, U.S. Pat. No. 5,456,713 discloses a graft prosthesis which is equipped with anchoring barbs on the end portions thereof, and incorporates apparatus for positioning the graft within a vessel lumen in order to repair an aneurysm. However, as in the previously described publications, there is no disclosure of the unique auastomotic structures which are attached to the opposite ends of the graft and which will enable the simple laproscopic emplacement thereof in the lumen of a patient for the repair of either a thoracic or abdominal aortic aneurysms.

European Patent Application Nos. EP 108666482; EP 1086663 A1; and EP 1086665 A1 are each directed to various types of apparatus or stents, wherein the apparatus is adapted to deliver and emplace a prosthesis, and wherein a tubular graft is formed over monofilament fibers having resilient portions for engaging the wall of the lumen.

In summation, none of the foregoing publications are adapted to provide the particular inventive prosthesis or system for the emplacement thereof in order to assist laproscopically in the repair of thoracic or abdominal aortic aneurysms.

SUMMARY OF THE INVENTION

The invention described herein involves a modification of an prosthesis by attaching anastomotic staples at each end of a graft, whereby no stent is required and no suturing is necessary, while the device can be delivered laparoscopically in a significantly shorter time period. Anastomotic staples comprised of shape memory metals or other suitable metals and alloys can be inserted through the distal ends of the graft, the graft everted over the staples, and the procedure completed by end-to-side anastomoses of the aorta and iliac arteries. Since the entire graft can be inserted in one piece, a second device to cover the contralateral iliac artery is not necessary.

In particular, as disclosed by an exemplary embodiment, the present invention is directed to an medical device comprising a vascular prosthesis which is a bifurcated aorta-iliac prosthesis having one end connected to the aorta, and lower or iliac branches leading away therefrom, with all ends of the vascular prosthesis being coupled to anastomosis devices. The graft-anastomosis device would be laparoscopically placed.

The inventive system which is utilized to repair aortic aneurysms is constituted essentially of a device which includes:

(a) A vascular prosthesis selectively comprised of textile, expanded PTFE, polyurethane, and other materials known to those skilled in the art of manufacturing vascular prostheses; with the prosthesis being configured as either a bifurcated or straight graft depending upon intended emplacement;

(b) Anastomotic coupling means attached to each end of the vascular prosthesis; with the coupling means being an annular member made from shape memory metal or a suture-based device;

(c) A device for providing visualization; with the device being comprised of insufflation means and a light source;

(d) A catheter, trocar, or other delivery instrument designed to contain the graft-anastomotic device in an undeployed state; deliver the graft-anastomotic device laparoscopically to the desired site of anastomoses with the aorta or iliac artery; and then deploy the graft-anastomotic device so that the aneurysm can be repaired; and (e) A vascular clamp, clip, or ligating suture such as LIGACLIP (reg. Trademark) adapted to exclude the aneurysm from blood flow after the aneurysm has been repaired.

The method which is utilized to repair the aneurysm and employing the above-mentioned system, includes:

(a) Providing a device for repairing an aortic aneurysm consisting of a vascular prosthesis precoupled to an anastomotic coupler or plurality of staples; with the device being housed in an undeployed state within a delivery means; such delivery means being a catheter or trocar;

(b) Creating at least one opening in a patient to obtain access to the abdominal, thoracic, or retroperitoneal space within the patient;

(c) Inserting the device referred to above into the patient; and (d) Repairing the aneurysm by connecting the vascular graft with anastomotic means to native vessels and clamping or ligating the aorta at at least one site distal to the most proximal anastomosis to exclude the aneurysm.

Accordingly, it is a primary object of the present invention to provide a system for repairing an aneurysm in a body vessel through the laparoscopic emplacement of an prosthesis consisting of a graft having anastomostic staples at each end thereof so as to obviate the need for stenting or suturing the affected body vessel.

Another object of the invention resides in the provision of a system for repairing an aneurysm in a body vessel through the emplacement of a graft having anastomostic staples at the ends thereof so as to obviate the need for stenting or suturing the affected body vessel.

Yet another object of the invention is to provide a device for laparoscopically emplacing an prosthesis in accordance with the system and method of repairing an aneurysm as described herein.

BRIEF DESCRIPTION OF THE ACCOMPANYING DRAWINGS

Reference may now be made to the following detailed description of preferred embodiments of the invention, taken in conjunction with the accompany drawings; in which:

FIG. 4 illustrates, generally diagrammatically, a delivery system and device for the emplacement of the prosthesis of FIG. 1A; and FIG. 5 illustrates, generally schematically, a representation of the endoprosthseis in the form of a bifurcated graft as in FIG. 1A, having been emplaced in order to repair an abdominal aortic aneurysm in a patient.

DETAILED DESCRIPTION OF PREFERRED EMBODIMENTS

Figure 1A:
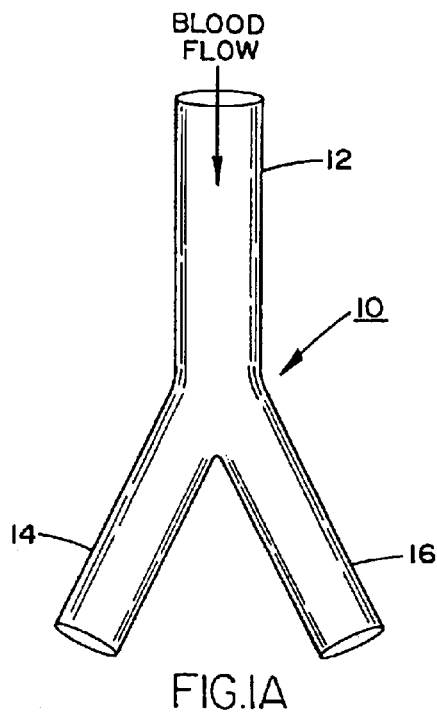
FIG. 1A illustrates, generally diagrammatically, a bifurcated aorta-iliac vascular prosthesis or graft.

Reverting specifically to FIG. 1A of the drawings, there is disclosed a graft or prosthesis 10 which, in this embodiment, is a bifurcated aorta-iliac vascular prosthesis having an upper segment 12 which is an aortic junction which faces the direction of incoming blood flow from the aorta, wherein the bifurcated lower end of the prosthesis 10 which is connected to the aorta segment 12 includes left and right iliac branches 14 and 16. This graft 10 may be readily constituted from a flexible material, such as for example, a textile, PTFE, biological materials, polyurethane, or hybrids thereof, as is widely known in the art of producing vascular prostheses.

Figure 1B:
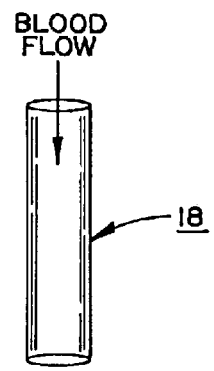
FIG. 1B illustrates a straight vascular prosthesis or graft.

The vascular graft or prosthesis of FIG. 1B of the drawings is similar to that of FIG. 1A; however, in this embodiment, the graft 18 is essentially tubular in nature. The materials which may be employed for this graft 18 are basically the same as those employed for the bifurcated graft 10.

Figure 2:
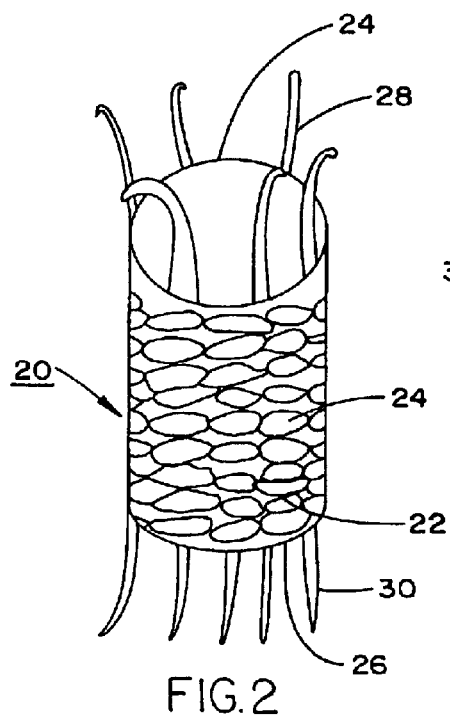
FIG. 2 illustrates an anastomotic coupler adapted to be utilized at either end of the vascular prosthesis or graft.

As illustrated in FIG. 2 of the drawings, there is diagrammatically shown a perspective view of an anastomotic coupler 20 which includes a tubularly shaped structure 22 consisting of cells 24 which allow for radial expansion and forming a compliant annular body. Preferably, the construction thereof is constituted of a shape memory metal or alloy material, such as stainless steel, nitinol (nickel-titanium alloy) or similar material, as is well known in the art. Moreover, the coupler body structure 22 can be formed of a suture-based device rather than a shape memory alloy. Attached to the opposite ends 24,26 of the annular compliant body 22 are vessel or graft engaging elements, such as axially and outwardly bent staples 28,30 which are spaced around the periphery of the body structure 22. These staples 28,30, may be constituted of nitinol, or of any suitable shape memory alloy material.

Figure 3:
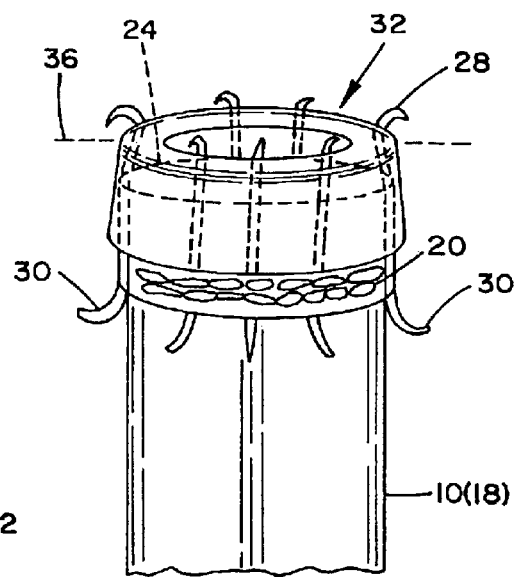
FIG. 3 illustrates the upper end of the graft connected to the wall of the aorta having the anastomotic coupler positioned on the vascular graft or prosthesis, which coupler has been attached to the everted end of the vascular prosthesis.

FIG. 3 of the drawings illustrates the upper end portion 32 of the vascular graft or endoprostheses 10 (or 18) with the anastomotic coupler 20 positioned thereover and having the end of the graft everted such that the staples 28 at the one end 24 of the coupler 20 pierce engagingly through the graft and the wall of the aorta 36, whereas the other staples 30 below the everted upper end portion of the graft are adapted engage into the wall of the body vessel.

The foregoing construction is also applicable to similar anastomotic couplers which are attached to the lower ends of, respectively the two iliac branches of the graft or prosthesis, as in FIG. 1A, or the lower end of the tubular vascular prosthesis or graft, as in FIG. 1B.

As illustrated in FIG. 4 of the drawings, this is schematically shown a delivery system and device 40 for emplacement of the graft 10. The prosthesis delivery device includes an essentially hollow tubular or cylindrical syringe-like or catheter member 41 having an axially movable handle 42 for pushing or deploying the device in the body vessel, with a rod member 43 extending towards the upper end of member 41 into engagement with the aortic anastomotic coupler 20, the staples 28 of which engage the wall of the aorta 36. Upon pushing the handle 42 into the cylindrical member 42 the entire prosthesis 10 located therein is by means of the rod member 43 deployed into the body vessel towards a surgical incision formed in the aorta for suitable emplacement.

As shown in FIG. 5, the upper end of the aortic anastomotic coupler 20 has the staples 28 engage into the aortic wall structure 36, whereas the lower bifurcated ends 14,16 of the vascular prosthesis is engaged into, respectively, the left and right iliac branches by means of iliac anastomotic couplers 50,52 which are essentially similar in construction to the aortic anastomotic coupler 20, although understandably of somewhat smaller sized diameters.

As shown in FIG. 5, the delivery system 40 of FIG. 4 is introduced through the wall 56 of a patient's body into the abdominal cavity 58, with a laparoscopic instrument and light source 60 extending towards the region of an aneurysm, and a further instrument and light source 62 extending into the region proximate the iliac anastomotic couplers 50,52.

The two laparoscopic instruments with light sources 60,62 which, respectively, are adapted to provide access to the aortic anastomotic coupler 20 and to the iliac anastomotic couplers 50,52 require only very small incisions to be formed in the body of the patient. This is also applicable to the incision required for the relatively small-sized delivery system or instrument 40 which includes the entire prosthesis, in effect; the preassembled graft 10 with the aortic and iliac anastomotic couplers 20,50,52 having all be previously attached to the graft body. Other laparoscopic instruments such as scissors, forceps, clamps, and clips can be used to assist in attaching the prosthesis to the aorta. Thus, it becomes readily apparent to one of skill in the art, that through the utilization a single system and delivery device it is possible to laparoscopically emplace or deploy an entire graft 10 (or 18) and anastomotic means preattached thereto in one piece, and in essentially a single procedure.

Although the foregoing description focuses on the use of the anastomosis system in thoraco-abdominal vascular surgery, the system is equally applicable to other situations which may require vessel anastomosis, including, but not limited to renal artery bypass grafting, femoral—femoral bypass and arterio-venous shunting, such as is commonly used for dialysis. Surgical anastomoses are also performed for various reasons on many different tubular organs of the body other than blood vessels, including the bowel, intestines, stomach and esophagus. While the devices and methods of the present invention are described herein as being intended primarily for vascular anastomoses, some or all of the embodiments could also be modified for performing end-to-side anastomoses on other tubular organs. Any one of the one or two-piece embodiments of the anastomosis staple device can be supplied preattached to a prosthetic graft vessel. For instance, the two-piece anastomosis staple device could be supplied in a kit, including a natural or artificial graft that is prepared with an anastomotic coupling member attached to one or both ends thereof, and one or two anchor members for attachment to the target vessel(s). Likewise, the one-piece anastomosis staple device can be supplied in a procedural kit preattached to a prosthetic graft vessel. This is equally applicable to artificial graft materials, such PTFE or Dacron (registered™) grafts, or to natural biological graft materials; including allografts of human graft vessels, or xenografts such as bovine or porcine graft vessels, either freshly harvested, glutaraldehyde treated or cryogenically preserved. An anastomotic device application or deployment instrument, such as those described above, could also be supplied in the procedural kit with one of the anastomotic devices already attached to the distal end of the instrument.

While the invention has been particularly shown and described with respect to preferred embodiments thereof, it will be understood by those skilled in the art that the foregoing and other changes in form and details may be made therein without departing from the spirit and scope of the invention.

What is claimed is:

1. A prosthesis for the extravascular endoscopic or laparoscopic repair of thoracic or abdominal aortic aneurysms; comprising:

a graft member constituting a vascular prosthesis; and
anastomotic coupling means each attached to respectively opposite ends of said graft member each said anastomotic coupling means including anastomotic staples, at least portions of said anastomotic staples of said coupling means forming vessel or graft member engaging elements extending through the wall of said vessel or graft member, whereby said prosthesis is unitarily deployable in the corporeal lumen of a patient so as to exclude the aneurysm, wherein said vascular prosthesis is a bifurcated aorto-iliac vascular prosthesis having an aortic segment and iliac branches of the graft member, wherein said anastomotic coupling means comprises anastomotic components which are deployed partially within the aorta and partially externally of the aorta of a patient.

2. A prosthesis as claimed in claim 1, wherein said anastomotic coupling means are fastened to respectively, the aortic segment of said vascular prosthesis for the attaching of the anastomotic staples thereof to the wall of the aorta, and fastened to the iliac branches of said bifurcated vascular prosthesis for the attaching of the anastomotic staples thereof to the iliac artery of a patient.

3. An extravascular laparoscopic or endoscopic method for repairing a thoracic or abdominal aortic aneurysm; comprising:

(a) providing a prosthesis for repairing the aortic aneurysm consisting of a vascular prosthesis precoupled to an at least one anastomotic coupler with a plurality of staples; the prosthesis being housed in an undeployed state within a delivery means; such delivery means being a catheter or trocar;

(b) creating at least one opening in a patient to obtain access to the abdominal, thoracic, or retroperitoneal space within the patient;

(c) inserting the delivery means into the patient; and (d) repairing the aneurysm by connecting the vascular graft with anastomotic means to the native vessel, at least portions of said anastomotic staples of said coupler forming vessel or graft member engaging elements extending through the wall of said vessel or grail member, and optionally clamping or ligating the aorta to exclude the aneurysm from blood flow.

4. A method as claimed in claim 3, wherein a graft member comprising said vascular prosthesis, and anastomotic couplers being each attached to respectively opposite ends of said graft member, each said anastomotic coupler including anastomotic staples, whereby said endoproshesis is unitarily deployable in the corporeal lumen of a patient so as to exclude the aneurysm from blood flow.

5. A method as claimed in claim 3, wherein each said anastomotic coupler comprises an annular member constituted of a shape memory metal.

6. A method as claimed in claim 4, wherein each said at least one anastomotic coupler is of a cell-like structure facilitating radial expansion thereof.

7. A method as claimed in claim 4, wherein said each at least one anastomotic coupler includes said anastomotic staples at each end thereof, wherein an end portion of the graft member is inserted into said anastomotic coupler and everted over said anastomotic staples into engagement therewith, said staples at one end of the anastomotic coupler engagingly piercing through the graft member and wall of the vessel and the staples below the everted upper end of the graft member are engaged into the wall of the vessel.

8. A method as claimed in claim 3, wherein said graft member composes a tubular element selected from the group of materials consisting of textiles, expanded PTFE, biological materials, polyurethane, and hybrids thereof.

9. A method as claimed in claim 3, wherein said vascular prosthesis is a bifurcated aorto-iliac vascular prosthesis having an sortie segment and iliac branches of the graft member, and said anastomotic coupling means comprising anastomotic components which are deployed partially within the aorta and partially externally of the aorta of a patient.

10. A method as claimed in claim 9, wherein said anastomotic coupling means couplers are fastened to respectively, the aortic segment of said vascular prosthesis for the attaching of the anastomotic staples thereof to the wall of the aorta, and fastened to the iliac branches of said bifarcated vascular prosthesis for the attaching of the anastomotic staples thereof to the iliac artery of a patient.

11. A method as claimed in claim 3, wherein said vascular prosthesis is a straight tubular prosthesis.

12. A method as claimed in claim 3, wherein said delivery means contains a pre-assembled said graft member and anastomotic couplers in an undeployed state preceding delivery of the vascular prosthesis to a required site of anastomosis with an aorta or iliac artery of a patient, said delivery means maintaining said prosthesis in readiness for deployment for the repair of an aneurysm.

13. A method as claimed in claim 12, wherein said delivery means comprises a syringe structure housing the undeployed vascular prosthesis, and axially movable pusher means for contacting said prosthesis for emplacement the prosthesis at a site for the repair of an aneurysm.

14. A method as claimed in claim 12, wherein said delivery means comprises a deploying rod connected to a loading end of said prosthesis for deploying the prosthesis in the body cavity of a patient.

15. A method as claimed in claim 12, wherein said delivery means includes an insufflation structure and a light source for visualization of the aneurysm repair site, and at least one surgical instrument selected from the group consisting of a scalpel, scissors, forceps, clamp and clip.

* * * * *

UNITED STATES PATENT AND TRADEMARK OFFICE
CERTIFICATE OF CORRECTION

PATENT NO. : 6,767,359 B2
DATED : July 27, 2004
INVENTOR(S) : Kevin Sean Weadock It is certified that error appears in the above-identified patent and that said Letters Patent is hereby corrected as shown below:

Column 8,
Line 12, please delete "composes" and insert -- comprises --.
Line 17, please delete "sortie" and insert -- aortic --.

Signed and Sealed this

Thirtieth Day of November, 2004

JON W. DUDAS
*Director of the United States Patent and Trademark Office*